(12) United States Patent
Heald (10) Patent No.: US 9,242,048 B2
(45) Date of Patent: Jan. 26, 2016

(54) MEDICATION DELIVERY DEVICE AND METHOD FOR DISPENSING A MEDICATION

(75) Inventor: Michael Heald, Maidenhead (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 310 days.

(21) Appl. No.: 13/513,814

(22) PCT Filed: Sep. 15, 2010

(86) PCT No.: PCT/EP2010/063506
§ 371 (c)(1),
(2), (4) Date: Oct. 4, 2012

(87) PCT Pub. No.: WO2011/032952
PCT Pub. Date: Mar. 24, 2011

(65) Prior Publication Data
US 2013/0041344 A1    Feb. 14, 2013

(30) Foreign Application Priority Data

Sep. 16, 2009  (EP) ..................................... 09170391

(51) Int. Cl.
*A61M 5/00* (2006.01)
*A61M 5/315* (2006.01)
*A61M 5/30* (2006.01)
*A61M 5/31* (2006.01)

(52) U.S. Cl.
CPC ....... *A61M 5/31525* (2013.01); *A61M 5/31573* (2013.01); *A61M 5/30* (2013.01); *A61M 5/31555* (2013.01); *A61M 5/31575* (2013.01); *A61M 5/31578* (2013.01); *A61M 5/31593* (2013.01); *A61M 2005/3125* (2013.01); *A61M 2005/3131* (2013.01); *A61M 2205/50* (2013.01)

(58) Field of Classification Search
CPC ............. A61M 2005/3125; A61M 2005/3131; A61M 2205/50; A61M 5/30; A61M 5/31525; A61M 5/31555; A61M 5/31573; A61M 5/31575; A61M 5/31578; A61M 5/31593
USPC .......................................... 604/208, 218, 222
See application file for complete search history.

(56) References Cited

U.S. PATENT DOCUMENTS

| | | | | |
|---|---|---|---|---|
| 1,707,880 | A * | 4/1929 | Sheets ........................... | 604/125 |
| 2,724,385 | A * | 11/1955 | Lockhart ....................... | 604/220 |
| 2,761,447 | A * | 9/1956 | Hersee ............... | 604/89 |
| 2,882,899 | A | 4/1959 | Nogier et al. | |
| 3,016,896 | A * | 1/1962 | Sickle ............................ | 604/89 |
| 3,506,008 | A * | 4/1970 | Huck ............................. | 604/193 |

(Continued)

FOREIGN PATENT DOCUMENTS

| | | |
|---|---|---|
| EP | 0279956 A1 | 8/1988 |
| EP | 1952836 A1 | 8/2008 |
| WO | 0205876 A2 | 1/2002 |

*Primary Examiner* — Aarti B Berdichevsky
(74) *Attorney, Agent, or Firm* — McDonnell Boehnen Hulbert & Berghoff LLP (57) ABSTRACT

A medication delivery device (100) comprises a container (101) for holding a medication (104) and a piston (102) which is at least partly arranged within the container (101) and which is axially displaceable with respect to the container (101). The piston (102) is at least partly arranged at a distance from an inner surface (112) of the container (101), thereby providing a channel (116) between the piston (102) and the container (101). The device (100) further comprises a seal (103), the seal (103) being arranged to limit the channel (116) proximally.

9 Claims, 3 Drawing Sheets

(56) References Cited

U.S. PATENT DOCUMENTS

| | | | |
|---|---|---|---|
| 3,672,369 A * | 6/1972 | Brown | 604/222 |
| 3,985,122 A | 10/1976 | Topham | |
| 5,512,054 A | 4/1996 | Morningstar | |
| 6,193,695 B1 | 2/2001 | Rippstein, Jr. | |

\* cited by examiner

MEDICATION DELIVERY DEVICE AND METHOD FOR DISPENSING A MEDICATION

CROSS REFERENCE TO RELATED APPLICATIONS

The present application is a 35 U.S.C. 371 National Application of PCT/EP2010/063506 filed Sep. 15, 2010, which claims priority to European Patent Application No. 09170391.8, filed Sep. 16, 2009, the entire contents of which are incorporated entirely herein by reference.

The present disclosure relates to a medication delivery device and a method for dispensing a medication.

Such medication delivery devices may have application where a person without formal medical training needs to administer an accurate and predefined dose of a medication. In particular, such devices may have an application where medication is administered on a regular or an irregular basis over a short term or long term period.

The published patent application WO 2002/05876 A2 describes a medication delivery device for administering multiple doses of medication. The accuracy of the amount of medication administered during dispensing of a dose should be as precise as possible, because a discrepancy between the set dose and the amount of medication which is actually delivered may have a negative effect on the user's health.

It is an objective to provide a medication delivery device and a method for dispensing medication which enable a simple and precise delivery of the medication.

This objective is achieved through the use of a delivery device according to claim 1 and a method. Advantageous embodiments are the subject matter of the dependent claims.

According to a first aspect, a medication delivery device comprises a container for holding a medication in a medication region. The container may have a proximal end and a distal end. The delivery device further comprises a piston which is at least partly arranged within the container. The piston may be displaceable with respect to the container, in particular in the distal direction, for dispensing a dose of the medication from the container. The medication delivery device may comprise a seal.

The piston is at least partly arranged at a distance from an inner surface of the container, thereby providing a channel between the piston and the container. The piston may be arranged at a distance from an inner surface of the container in a radial direction. The channel extends, preferably axially, along the piston. The channel is in fluid communication with the medication region. The seal is arranged to limit the channel, in particular to limit the channel proximally. The piston is displaceable, in particular axially displaceable and/or displaceable in the distal direction, with respect to the seal.

This has the advantage that simple and precise usage of the medication delivery device is facilitated. A user may administer a number of preset or user-settable doses of the medication. Since the piston is moveable with respect to the seal and the piston does not need to be in leak-proof direct contact with the container, the amount of medication which is dispensed from the container may be largely independent of an unevenness that an inner surface of the container may have. In particular, the volumetric accuracy of medication which is dispensed from the container may be governed by the dimensional stability of the piston. That is to say, if the piston is very finely toleranced, the dose accuracy will be high. Problems often arising in cartridges which have a piston that circumferentially contacts the bore of the cartridge for sealing the medication within the cartridge, like weeping of medication from the cartridge or inaccurate dose delivery due to relaxation of the deformed piston may be reduced or even avoided.

The seal may be secured against movement with respect to the container. The seal may be fixed to the container. The seal may be arranged at the proximal end of the container. This has the advantage that the medication delivery device is easy to assemble and that a precise usage of the medication delivery device is enabled. The container may have an outlet for dispensing medication from the container. The outlet may be provided at a distal end of the container.

A length of the channel may increase when the piston is displaced in the distal direction with respect to the seal.

The seal may surround the piston laterally. The seal may be annular.

The piston may be capable of exerting a pressure on the medication during and/or for dispensing of the dose. The medication may transfer at least a part of the pressure on the seal. A mounting of the seal to the container may be capable of, in particular the mounting may be configured to be capable of, resisting the pressure exerted by the medication on the seal when dispensing the dose.

The seal may comprise an opening. A cross-section of the opening may be adapted to a cross-section of the piston. The cross-section of the opening may be adapted to the cross-section of the piston, such that the seal and the piston comprise a common contact area.

At least that part of the piston which is intended to be guided through the seal during dispensing of the dose preferably comprises a constant cross-section along its longitudinal axis.

In an embodiment, the piston comprises a rigid core and an outer shell. The outer shell may surround the rigid core. The outer shell may be in contact with the seal. The outer shell may be made from a material different from the material of the core. The outer shell may be made from a material which is less rigid than the core. The outer shell may be a thin film. The compressibility of the piston is expediently governed by the rigid core, even if a flexible material is used for the outer shell. However, the outer shell may improve the leak tightness between the piston and the seal.

In another embodiment, the piston is hollow. The piston may comprise an opening. The opening may be arranged on that side of the piston that faces away from the medication region. The hollow within the piston may be accessible via the opening. The opening may be arranged at the proximal end of the piston. The medication is expediently prevented from entering the hollow by a wall of the piston. An inner surface of the piston, in particular an inner surface of the wall of the hollow, may be provided with a drive means, for example a thread, preferably a helical thread.

The medication delivery device may comprise a drive mechanism. The drive mechanism is expediently configured to drive the piston for dose delivery. The drive means within the piston may be provided for interaction with the drive mechanism, for example with a piston rod. The piston rod may abut and/or engage the drive means. The piston rod and the drive means may be threadedly engaged.

The container which holds the medication may be a syringe or a cartridge. The medication may be sealed within a pre-filled cartridge.

A method for dispensing a medication comprises providing a container that holds a liquid medication. A displacement volume is introduced into the liquid medication. Thereby, a volume of the liquid medication is displaced. A volume of the liquid medication is dispensed from the container. The dispensed volume may be less than or equal to the displacement volume and/or less than or equal to the displaced volume of medication. For example, the dispensed volume of medication may be less than the displacement volume if there is gas enclosed within the container and the gas has to be either displaced or compressed before medication may leave the container. Otherwise, the dispensed volume may be equal to the displacement volume. In each case, the dispensed volume may be defined by the displacement volume.

By defining the volume of dispensed medication by a volume introduced into the medication instead of solely by the distance a piston is displaced distally with respect to the container, the dose accuracy can be increased.

The method may comprise introducing at least a part of a displacement member into the liquid medication. This part of the displacement member may determine the displacement volume. A volume of the liquid medication which is less than or equal to the volume enclosed by the introduced part (this volume may determine the displacement volume) of the displacement member may be dispensed. The method may comprise increasing the part of the displacement member that is arranged in the liquid medication, so as to further dispense medication.

In an embodiment, the displacement member may be a piston, in particular the piston as it was described further above and is described in more detail below. The displacement volume may be the volume enclosed by the newly introduced part of the displacement member into the medication. The displacement volume may be the volume of the part of the displacement member which is newly introduced into the medication.

The method may comprise setting of a dose volume of the liquid medication to be dispensed. The displacement volume may be introduced into the liquid medication until the displaced volume (which may be equal to the displacement volume) essentially equals the dose volume. The displacement volume may be introduced into the liquid medication until the displaced volume is 90% or more, preferably 99% or more, of the dose volume. The displacement volume may be introduced into the liquid medication until the displaced volume is 95% or more, preferably 99.5% or more, of the dose volume. The discrepancy of the dispensed amount of the liquid medication and the set dose may be two percent or less, preferably one percent or less, in relation to the set dose.

The method according to the present application is preferably not intended to or used to treat the human or animal body by surgery or therapy and diagnostic methods practised on the human or animal body. The method may be suitable for the purpose of testing, for example for testing a medication delivery device in a laboratory environment.

Herein below the embodiments will be described in more detail in conjunction with the appended drawings.

Figure 1A:
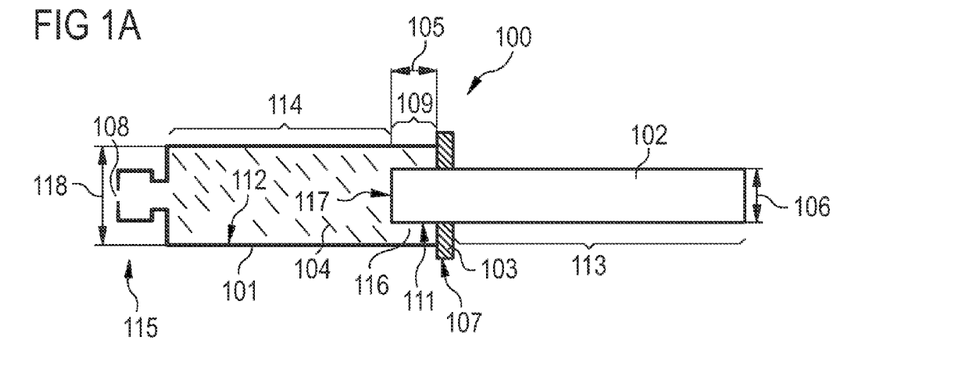
FIG. 1A schematically shows a medication delivery device according to an embodiment in a first, container full, state, FIG. 1B schematically shows the medication delivery device in a second state, where some medication has already been delivered, FIG. 2 schematically shows a medication delivery device according to a further embodiment, FIG. 3 schematically shows a piston according to an embodiment, FIG. 4 schematically shows a piston according to a further embodiment, and FIG. 5A schematically shows a sectional view along line A-A' of FIG. 1B, FIG. 5B schematically shows a sectional view along line B-B' of FIG. 1B, FIG. 6 schematically shows a sectional view of a piston with an outer shell according to an embodiment.
Figure 1B:
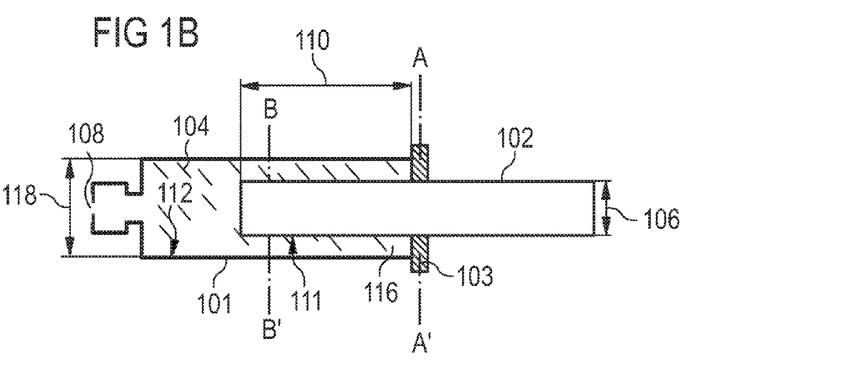

In FIGS. 1A and 1B an embodiment of a medication delivery device 100 is schematically shown.

The medication delivery device 100 comprises a container 101. Medication 104 is retained in the container 101. The medication 104 is preferably liquid medication. The container 101 preferably contains a plurality of doses of the medication 104. The medication 104 may comprise insulin, heparin or growth hormones, for example. The container 101 has an outlet 108 at its distal end 115. Medication 104 can be dispensed from the container through the outlet. The device 100 may be a pen-type device, in particular a pen-type injector. The device 100 may be a disposable or a reusable device. The device 100 may be a device configured to dispense fixed doses of the medication or variable, preferably user settable, doses. The device 100 may be a needle-based or a needle-free device. The device 100 may be an injection device.

The term "distal end" of the medication delivery device 100 or a component thereof, in particular the container 101, may refer to that end of the device or the component which is closest to the dispensing end of the device 100. The term "proximal end" of the medication delivery device 100 or a component thereof may refer to that end of the device or the component which is furthest away from the dispensing end of the device. In FIG. 1, the "distal end" of the device 100 was assigned reference numeral 115 and the "proximal end" was assigned reference numeral 107.

A piston 102 is retained at least partly within the container 101. The piston 102 is displaceable with respect to the container. The piston 102 is moveable with respect to the container 101 in the distal direction. Such a movement may cause medication 104 to be dispensed from the container 101 through the outlet 108 during operation of the device. The piston 102 comprises a part 109 which is disposed within the container 101. A further part 113 of the piston 102 is disposed outside the container 101.

A seal 103 is arranged to seal the interior of the container proximally. The seal is capable of providing a leak-proof coupling to the piston 102. The boundary between piston and seal is preferably fluid-tight. Expediently, no medication may pass through a boundary between piston and seal during dispensing operation and/or when the device is in storage position. The seal 103 is preferably non-displaceable, e.g. immovable, with respect to the container 101, particularly during dispensing of medication. The piston 102 is displaceable with respect to the seal 107. The piston may be in frictional contact with the seal during dispensing operation. In the embodiment according to FIG. 1A the part of the piston 102 which is arranged at the distal side of the seal is the part 109. The part of the piston 102 which is arranged at the proximal side of the seal is the part 113.

The seal may comprise or consist of a plastic material. The seal may comprise an elastomer, like Bromobutyl Rubber for example. The piston may comprise or consist of a plastic material, for example a polymer, preferably a medical grade polymer, a metal, for example stainless steel, a glass or a ceramic material. The piston may be rigid. The piston may comprise a material of low compressibility. Expediently, the compressibility of that material of low compressibility governs the compressibility of the piston. The material of low compressibility may have a compressibility which is less than a compressibility of the seal. Preferably, the piston is incompressible.

The part 109 and/or the piston 102 comprise a cross-section 106. The cross-section 106 of the piston 102 is essentially perpendicular to the longitudinal direction of the piston 102.

The part 109 and/or a part of the piston that is intended to be guided through the seal, in particular intended to be guided into the medication, is adapted to be circumferentially arranged at a distance from the container bore. The cross-section of the piston 102 will in a preferred embodiment be constant along its longitudinal axis or at least partly along its longitudinal axis, preferably along the part of the piston that is intended to be guided through the seal. The cross-section 106 of the part 109 and/or the piston 102 is smaller than a cross-section 118 of the interior of the container 101. The cross-section 118 is the inner cross-section of the container 101. The cross-section 118 of the container 101 is essentially perpendicular to the main longitudinal direction of extent of the container 101.

Since the cross-section 106 is smaller than the cross-section 118, a side surface 111 of the part 109 of the piston 102 and an inner surface 112 of the container 101 are arranged at a distance with respect to one another. The surface 111 and the surface 112 are arranged at a distance with respect to one another circumferentially. A fluid channel 116 is provided between the part 109 and the inner surface 112. The fluid channel 116 may surround the part 109.

The fluid channel 116 is in fluid communication with a medication region 114. The medication 104 is mainly arranged in the medication region 114 of the container 101. The medication region 114 is a region of the interior of the container 101. In particular, the medication region 114 is a distal region of the interior of the container 101. Medication may flow from the medication region 114 into the fluid channel 116. The fluid channel 116 is filled with medication. The medication may be in immediate contact with piston, seal and/or container, in particular in the region of the fluid channel. Piston, seal and/or container may limit the channel which is open on the side of the medication region Since medication which is arranged inside the channel 116 will not be dispensed from the container, as it will become apparent from the discussion below, the distance between the part 109 and the inner surface 112 is preferably as small as possible. Accordingly, the fluid channel 116 is preferably slim, in particular such as compared to the extent of the medication region. The width of the channel 116 is expediently chosen so as to avoid frictional contact or sealing contact between piston 102 and container 101.

To form the proximal end of the channel 116, the seal 103 is immovably connected to the container 101. The seal 103 surrounds the piston 102 at least partly, preferably completely circumferentially. The seal 103 and the piston 102 are sealably and preferably frictionally connected. The fluid medication 104 is prevented from leaving the container 101 via the proximal end 107 by the seal. For this purpose, the seal 103 is fixed to the container 101. The seal 103 is secured against axial and rotational movement with respect to the container 101. At the proximal end of the channel 116 the medication 104 is in direct contact with the seal 103.

By advancing the piston 102 axially in the distal direction with respect to the seal 103 and the container 101, medication may be displaced and dispensed from the container.

FIG. 1B shows the piston 102 displaced in the distal direction with respect to seal and container as compared to the situation shown in FIG. 1A. The part of the piston 102 which is arranged inside the medication 104 is larger than in FIG. 1A. A distance 110 from a distal end surface 117 of the piston 102 to the seal 103 is greater than the corresponding distance 105 in FIG. 1A.

The amount of dispensed medication corresponds to the volume of the part of the piston 102 newly inserted into the medication region 114 by displacing the piston 102. The piston is introduced into the medication until the displaced volume of medication equals the desired and/or set volume of medication. The volume of the piston 102 newly inserted into the medication region 114 is determined by the cross-section 106 and the axial displacement of the piston 102 with respect to the seal 103, for instance the difference between the distance 105 and the distance 110. The volume of the amount of the dispensed medication is essentially equal to the volume of the part of the piston 102 which is additionally introduced into the medication 104.

By introducing a defined volume (displacement volume) into the medication, a volume of medication 104 may be dispensed which is equal to the defined volume. By displacing the piston 102 distally with respect to the seal 103 the part 109 of the piston 102 which is arranged in the medication 104 is increased. Simultaneously, the part 113 of the piston 102 arranged outside of the medication 104 is reduced. Thereby, the volume of the piston 102 arranged inside the medication 104 may be increased. Since the dimensions of the piston 102 are well-known, the additionally inserted volume is well-known. By increasing the volume of the piston arranged at the distal side of the seal, the volume of medication region available to be occupied by the medication is reduced.

The dispensed amount of medication corresponds to the additionally inserted volume of the piston. The dispensed amount of the medication is independent of the shape of the container 101. Particularly, volumetric accuracy of the dispensed amount of medication may be isolated against, protected from and/or independent of irregularities arising from variations of the shape of the container, in particular the inner cross-section, for example variations of the diameter. Usually, the inner surface 112 of the container 101 is not constant but comprises significant irregularities. Variations of the shape of the container may result from fabrication tolerances. Since, presently, the amount of dispensed medication may only depend on the dimensions of the piston, particularly on the volume of the piston newly inserted into the medication, the shape of the container may be irrelevant for the accuracy of the dispensing of medication. The discrepancy of the dispensed volume of medication and a set dose volume of medication may be five percent or less. In another embodiment the discrepancy is two percent or less, one percent or less or even 0.5 percent or less. Manufacturing defects in the container advantageously do not influence the dispensed amount of medication which may be determined by the volume of that part of the piston which is newly introduced into the medication. If, in contrast thereto, a piston was used which circumferentially is in immediate contact with the container and thus simultaneously serves as a "seal", the dispensed amount considerably depends on variations in the container diameter.

When displacing the piston 102 distally with respect to the seal 103 and the container 101 to dispense medication, a pressure is exerted on the medication 104. During the first use of the medication delivery device displacing the piston may displace medication from the medication region 114 and press the displaced medication into the channel 116. Prior to the first use, the medication region 114 and/or the channel 116 may be at least partly filled with air. The air may be removed out of the container by the first dispensing operation of the device, for example by a priming operation. Alternatively, the channel may be filled with medication before the first operation is commenced. The medication in the channel 116 which was or is already filled with medication exerts a pressure on the seal 103 during dispensing of medication. The pressure exerted by the medication on the seal 103 is equal to the pressure exerted by the piston 102 on the medication 104 during dispensing of medication.

The mounting of the seal 103 at the container 101 is capable of resisting the pressure exerted by the medication 104 during delivery of medication. The pressure inside the container increases during displacement of the piston 102 until medication is dispensed through the outlet of the container 101. The container 101 and the seal 103 are formed, such that the exerted pressure may be relieved by dispensing medication through the outlet of the container. The piston 102 keeps its volume even under the pressure during dispensing of medication. The piston 102 is preferably so rigid that the piston 102 is not or not significantly deformed even under the pressure acting on the piston during dispensing of medication. The container and the seal are not substantially deformed by the exerted pressure during dispensing of medication.

Figure 2:
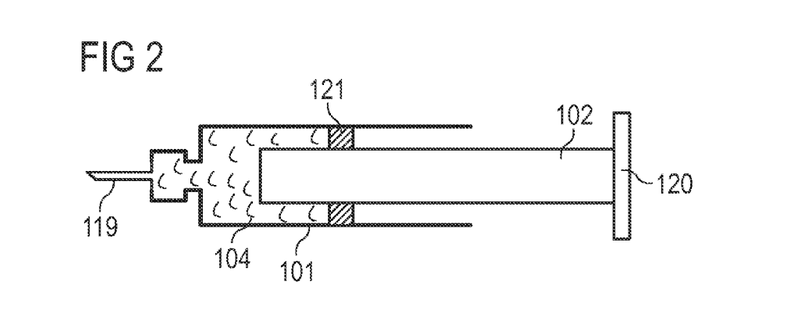

In contrast to the embodiment according to FIGS. 1A and 1B the medication delivery device according to the embodiment of FIG. 2 does not comprise the seal 103 arranged at the proximal end 107 of the container 101.

Rather, in the embodiment of FIG. 2 a seal 121 is arranged inside the container 101. An outer surface of the seal 121 may be attached to an inner surface of the container, preferably permanently attached. Further, the embodiment according to FIG. 2 comprises a needle device 119. The embodiment according to FIG. 2 further comprises a drive mechanism 120.

The needle device 119 is attached to the container 101 at the distal end 115 of the container. The needle device 119 is in fluid communication with the medication region 114 and the outlet 108 of the container. Medication may be dispensed from the container through the needle device 119. Medication may be administered hypodermically through the needle device by a user.

The drive mechanism 120 may comprise means for setting the dose to be administered. The drive mechanism 120 may further comprise means for transferring an axial movement through/within the medication delivery device, preferably from an actuating means to the piston 102. The drive mechanism may comprise a piston rod (not explicitly shown), which is adapted to drive the piston in the distal direction. A distal end face of the piston rod may be arranged to drive, preferably to abut, the proximal end face of the piston. The drive mechanism may be releasably coupled with the piston. The drive mechanism may comprise a gearing and/or an electric actuator.

The container may be a cartridge, which may be pre-filled with medication. Alternatively, the container may be a syringe-type container.

During operation of the medication delivery device 100, a user may set a desired dose of medication 104 which should be dispensed from the container 101. Dose setting may comprise setting of a dose volume of medication to be dispensed. To dispense the dose volume of medication, the user may actuate the drive mechanism of the medication delivery device, for example by manually exerting a force on the drive mechanism 120, for example on a dose button (not explicitly shown) of the drive mechanism. This force is transferred to the piston 102, for instance by the piston rod. The force may be transferred directly to the piston 102 or via an electric actuator and/or a gearing.

Due to the exerted force, the piston 102 is displaced with respect to the seal 121. The piston 102 is displaced with respect to the seal 121, such that it is moved into the medication. The piston 102 is moved by a distance in the distal direction which corresponds to the dose of medication to be dispensed. The piston is displaced, such that a displacement volume of the piston is inserted into the medication. The displacement volume is substantially equal to the volume of the amount of the medication which is subsequently dispensed. If the medication delivery device is a multi-dose delivery device, the piston can be moved several times in the distal direction with respect to the seal to replace a further volume of medication and to dispense the further volume of medication from the container.

The volume of the part of the piston which is newly introduced into the medication during each discrete dose dispensing operation may be fixed such that a fixed dose is delivered by the medication delivery device during each dose dispensing operation. In an embodiment, the medication delivery device is a fixed dose device.

In another embodiment, the volume of the part of the piston 102 which is inserted in the medication 104 during each dose dispensing operation may vary and correspond to a dose set by a user via the dose setting means. In an embodiment, the medication delivery device is a variable dose device.

The device may be of any shape, for instance compact or pen-type. Furthermore, the said device may be needle-free. In particular, the medication delivery device may be a disposable needle-based pen-type device providing multiple predefined doses. The medication delivery device is designed for use by persons without formal medical training.

The device may comprise further elements (not shown), for example sensors and/or electronic circuits. The device may comprise a display for providing information to the user. The information may comprise information about the number of doses of medication remaining in and/or the number of doses dispensed from a given container.

The term "piston rod" shall preferably mean a component adapted to operate through/within the housing, designed to transfer axial movement through/within the medication delivery device, preferably from the drive member to the piston, preferably for the purpose of discharging/dispensing an injectable product. The piston rod may be flexible or not. It may be a simple rod, a lead-screw, a rack and pinion system, a worm gear system, or the like. The term "piston rod" shall preferably further mean a component having a circular or non-circular cross-section. It may be of unitary or multipart construction.

The medication delivery device may comprise further elements, for example a housing. The term "housing" shall preferably mean any exterior housing ("main housing", "body", "shell") or interior housing ("insert", "inner body"), which may have a unidirectional axial coupling to prevent proximal movement of specific components. The housing may be designed to enable the safe, correct, and comfortable handling of the medication delivery device or any of its mechanisms. It may be designed to house, fix, protect, guide, and/or engage with any of the inner components of the medication delivery device (for instance seal, container, piston) by limiting the exposure to contaminants, such as liquid, dust, dirt etc. In general, the housing may be unitary or a multipart component of tubular or non-tubular shape. Usually, the exterior housing serves to house a container from which a number of doses of a medicinal product may be dispensed.

The medication may comprise insulin, for example rapid-acting, short-acting, intermediate-acting or long-acting insulin, growth hormones, low molecular weight heparins, and/or their analogues and/or derivatives etc. The term "insulin" could mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Furthermore, the device may comprise a needle or may be needle-free. In particular, the medication delivery device may be a disposable needle-based pen-type device providing multiple pre-defined doses having mechanical and manual dose setting and dose delivery mechanisms, which is designed for use by persons without formal medical training such as patients including children and adults. The device may comprise electrical dose setting and dose delivery mechanisms. Preferably, the medication delivery device is of the injector-type.

Figure 3:
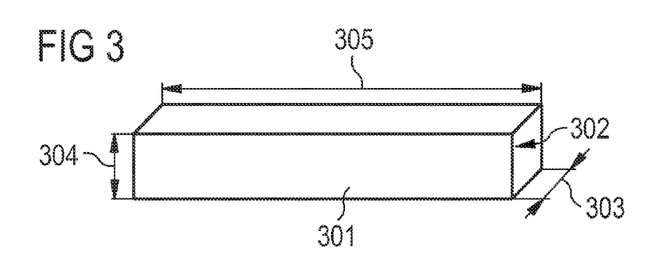

FIG. 3 schematically shows an exemplary embodiment of a piston 301 which may be used in a medication delivery device according to the present disclosure. The piston 301 comprises a surface 302 which comprises a first edge 303 and a second edge 304. The second edge 304 is essentially perpendicular to the first edge 303. A third edge 305 is essentially perpendicular to the first and the second edge. The piston 301 basically comprises a cuboid shape. The volume of the piston is determined by the length of the three edges 303, 304, 305. The axial direction of the piston may extend along the longest edge of the piston, for example along the edge 305. The piston may be a hollow body or may be a solid body.

The displacement volume of the piston is determined by the length of the edge 303 and the length of the edge 304 as well as the part of the piston 301 which extends along the edge 305 and is introduced into the medication.

Figure 4:
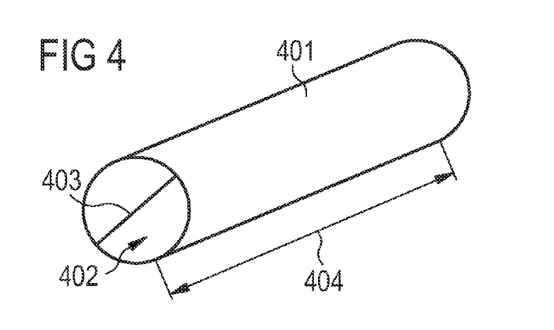

FIG. 4 shows a further exemplary embodiment of a piston 401 which may be used in a medication delivery device according to the present disclosure. The piston comprises an essentially cylindrical shape, the volume of which is determined by diameter 403 and length 404. The piston may be a hollow body or may be a solid body. A surface 402 runs perpendicularly to the longitudinal axis of the piston.

The displacement volume of the piston 401 is determined by the diameter 403 as well as the part of the piston 401 which extends along the length 404 and is introduced into the medication.

Figure 5A:
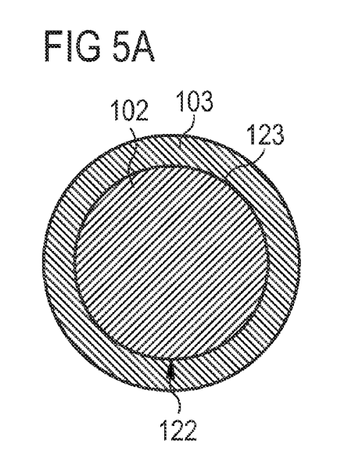

FIG. 5A shows a cross-sectional view of the medication delivery device 100 along a line A-A' as shown in FIG. 1B. The piston 102 is arranged in an opening 122 of the seal 103. The cross-section of the piston 102 and the cross-section of the opening 122 are adapted to each other such that the piston and the seal comprise a common contact area 123. The cross-section of the piston 102 and the cross-section of the opening 122 are adapted to each other such that the piston and the seal are in contact with each other. The seal entirely surrounds the piston in the shown cross-sectional view. The piston comprises a circular cross-section and the seal comprises a ring like shape. The piston and the seal are coupled such that no medication can pass through the coupling at the common contact area 123. The coupling of the piston and the seal at the common contact area 123 is leak-proof.

Figure 5B:
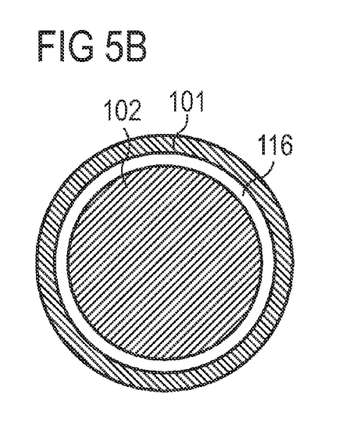

FIG. 5B shows a cross-sectional view of the medication delivery device 100 along the line B-B' as shown in FIG. 1B. The container 101 surrounds the piston 102 such that the channel 116 is formed between the container and the piston. The channel can be filled with medication during operation of the medication delivery device or may already be filled with medication before the device is primed. The channel is proximally limited by the seal. The shape of the piston is adapted to the shape of the container such that the channel may be formed between the container and the piston. Due to the adaptation of the cross-section of the piston and the cross-section of the interior of the container to one another the channel is preferably as small as possible. Thus, after having dispensed the last dose, a minimal amount of medication remains in the channel and in the container.

Figure 6:
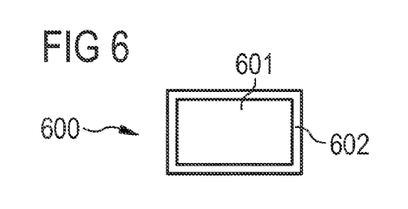

FIG. 6 schematically shows a sectional view of a piston 600 according to a further embodiment.

The piston 600 comprises a core 601 and an outer shell 602 surrounding the core 601. The outer shell 602 may comprise a material different from the material which the core comprises. The material of the outer shell may be more flexible and elastic than the material comprised by the core 601. However, the compressibility of the piston may still be governed by the rigid core. The outer shell may improve the tightness of the connection between the seal and the piston for sealing the container proximally. The outer shell may be a thin film, e.g. with a thickness of 1 mm or less, like 0.5 mm or less, 0.2 mm or less, or 0.1 mm or less. The core 601 is sufficiently rigid and inflexible as to resist against deformation which may occur during administering of medication if a different piston was used. The core 601 is sufficiently rigid and inflexible as to resist the pressure which may be affected during dispensing medication.

During operation, the outer shell 602 is in contact with the seal which is fixed to the medication container as described in connection with FIG. 1A, 1B, 2 or 5A. The contact of the seal and the outer shell is very tight and highly leak-proof. Thus, the coupling of the piston 600 with the seal is very leak-proof. Due to the stiff core, the piston 600 may hardly be deformed during the administration of medication such that dose accuracy can be increased. The piston 600 keeps its original shape and/or volume even during dispensing of medication. During operation, a volume of medication substantially equal to the additional volume of the piston that is introduced into the medication will be dispensed from the container. The additionally introduced volume of the piston 600 may be determined by the volume enclosed by the outer shell 602.

The outer shell 602 surrounds the core 601, preferably at least circumferentially, or may cover more parts of the surface of the core 601, in particular those parts which are already or may be arranged inside the medication. The outer shell may be made from a material which is more suitable to come into direct contact with the medication than the material of the core. In FIG. 6, the cross-section of the piston 600 is shown to be rectangular. In other embodiments, the cross section of the piston may comprise a different design. The cross-section of the piston may comprise a circular core surrounded by a ring-like outer shell for example.

Figure 7:
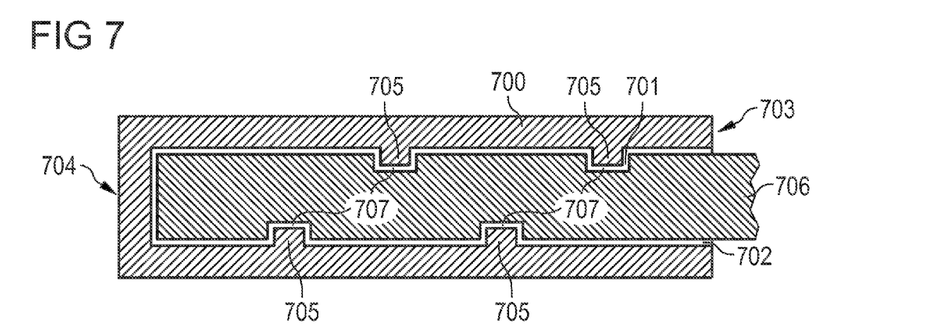
FIG. 7 schematically shows a sectional view of a piston with a hollow according to an embodiment.

FIG. 7 shows a piston 700. The piston 700 has a hollow 701. An opening 702 is provided. The opening 702 provides access to the hollow 701. Opening 702 may be provided at the proximal end 703 of the piston 700. The hollow 701 is expediently only accessible through the proximal opening 702. In particular, the hollow 701 is preferably non-accessible from the distal end 704 of the piston 700. Medication may thus be prevented from entering the hollow and leaving the container and piston unintentionally via opening 702. Within hollow 701, a drive means 705, for example a male or female thread, preferably a helical thread, is provided.

A drive member 706, e.g. a piston rod, is arranged within the hollow 701. The drive member 706 is preferably part of a drive mechanism of the medication delivery device, for example part of the drive mechanism 120 which was described previously. The drive member 706 is expediently provided to interact with drive means 705 and, in particular, to transfer force to the piston, which advances the piston with respect to the corresponding seal (not explicitly shown in FIG. 7). The drive member and the drive means may be designed to engage and/or to abut. The drive member 706 may be threadedly engaged with the piston 700. For this purpose, a thread 707, which may be a male or a female thread, preferably a helical thread, may be provided in the drive member 706, in particular on an inner wall of the hollow 701.

The term medication, as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The scope of protection of the invention is not limited to the examples given hereinabove. The invention is embodied in each novel characteristic and each combination of characteristics, which particularly includes every combination of any features which are stated in the claims, even if this feature or this combination of features is not explicitly stated in the claims or in the examples.

REFERENCE NUMERALS 100 medication delivery device
101 container
102 piston
103 seal
104 medication
105 distance I
106 cross-section
107 end
108 outlet
109 part
110 distance II
111 surface
112 surface
113 part
114 medication region
115 end
116 channel
117 surface
118 cross-section
119 needle device
120 drive mechanism
121 seal
122 opening
123 contact area
301 piston
302 surface
303 edge I
304 edge II
305 edge III
401 piston
402 surface
403 cross-section
404 length
600 piston
601 core
602 outer shell
700 piston
701 hollow
702 opening
703 proximal end
704 distal end
705 drive means
706 drive member
707 thread

The invention claimed is:

1. A medication delivery device, comprising:
   a container for holding a medication in a medication region, the container having a proximal end and a distal end,
   a piston which is at least partly arranged within the container and which is displaceable with respect to the container in the distal direction for dispensing a dose of the medication from the container, and
   a seal, wherein
   during dispense of the dose of the medication from the container, the piston is at least partly arranged at a distance from an inner surface of the container, thereby providing a channel between the piston and the container, the channel extending along a side surface of the piston and being in fluid communication with the medication region, and a length of the channel increases when the piston is displaced in the distal direction with respect to the seal,
   the seal is arranged to limit the channel proximally, and
   the piston is displaceable in the distal direction with respect to the seal, wherein the seal is secured against movement with respect to the container.

2. The medication delivery device according to claim 1, wherein the seal is fixed to the container.

3. The medication delivery device according to claim 1, wherein the seal is arranged at the proximal end of the container.

4. The medication delivery device according to claim 1, wherein the seal is annular and surrounds the piston laterally.

5. The medication delivery device according to claim 1, wherein:
- the piston is capable of exerting a pressure on the medication for dispensing of the dose, wherein
- the medication transfers at least a part of the pressure on the seal, and
- a mounting of the seal at the container is capable of resisting the pressure exerted by the medication on the seal when dispensing the dose.

6. The medication delivery device according to claim 1, wherein:
- the seal comprises an opening, and
- a cross-section of the opening is adapted to a cross-section of the piston such that the seal and the piston comprise a common contact area.

7. The medication delivery device according to claim 1, wherein at least the part of the piston which is intended to be guided through the seal during dispensing of the dose comprises a constant cross-section along its longitudinal axis.

8. The medication delivery device according to claim 1, wherein the piston comprises a rigid core and an outer shell, the outer shell being less rigid than the core.

9. The medication delivery device according to claim 1, wherein the piston is hollow and has an opening at its proximal end.

* * * * *